United States Patent
Wilhelm et al.

(10) Patent No.: US 7,241,627 B2
(45) Date of Patent: Jul. 10, 2007

(54) WEARABLE ARTICLE WITH MULTI-LEVEL ALERT SYSTEM

(75) Inventors: Hoa La Wilhelm, Appleton, WI (US); Dave Allen Soerens, Neenah, WI (US); Lee Delson Wilhelm, Appleton, WI (US); James Hongxue Wang, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 619 days.

(21) Appl. No.: 10/683,789

(22) Filed: Oct. 10, 2003

(65) Prior Publication Data

US 2005/0079637 A1      Apr. 14, 2005

(51) Int. Cl.
*G01N 33/543* (2006.01)

(52) U.S. Cl. .............. 436/518; 436/528; 436/529; 422/50; 422/55; 422/56; 422/57; 422/61; 422/68.1; 422/82.05; 435/283.1; 435/287.7; 435/288.7

(58) Field of Classification Search .......... 435/283.1, 435/287.1; 422/50, 55, 56, 68.1, 69, 119; 436/2, 43
See application file for complete search history.

(56) References Cited

U.S. PATENT DOCUMENTS

| | | | |
|---|---|---|---|
| 3,917,452 A | * | 11/1975 | Rittersdorf et al. ........... 436/66 |
| 4,063,754 A | | 12/1977 | Shackle et al. |
| 4,518,547 A | | 5/1985 | Cuff et al. |
| 5,468,236 A | | 11/1995 | Everhart et al. |
| 5,916,969 A | | 6/1999 | Wang et al. |
| 6,001,658 A | | 12/1999 | Fredrickson |
| 6,075,118 A | | 6/2000 | Wang et al. |
| 6,203,496 B1 | | 3/2001 | Gael et al. |
| 6,541,030 B2 | | 4/2003 | Vaghefi |
| 6,583,722 B2 | * | 6/2003 | Jeutter et al. ............ 340/573.1 |
| 6,617,488 B1 | * | 9/2003 | Springer et al. ............ 604/361 |
| 2003/0065299 A1 | * | 4/2003 | Carlucci et al. ....... 604/385.01 |
| 2003/0158530 A1 | | 8/2003 | Diehl et al. |

FOREIGN PATENT DOCUMENTS

| | | |
|---|---|---|
| DE | 196 23 747 A1 | 12/1997 |
| WO | WO 01/50996 A1 | 7/2001 |
| WO | 03/070137 | 8/2003 |

OTHER PUBLICATIONS

Ponce et al. Critical Revision of Presumptive Tests for Bloodstains. Forensic Science Communications, vol. 1, No. 2, Jul. 1999. (no page numbers).*
US 6,294,646, 09/2001, Wang et al. (withdrawn)

* cited by examiner

Primary Examiner—Long V. Le
Assistant Examiner—Melanie J. Yu
(74) Attorney, Agent, or Firm—Pauley Petersen & Erickson

(57) ABSTRACT

A wearable article equipped with a multi-level alert system detects and emits signals corresponding to various abnormal levels of a substance in a mammalian extract. By providing different signals corresponding to multiple abnormal levels of the substance, the wearer is simultaneously alerted to the existence of an abnormality, and informed of the level of severity.

26 Claims, 2 Drawing Sheets

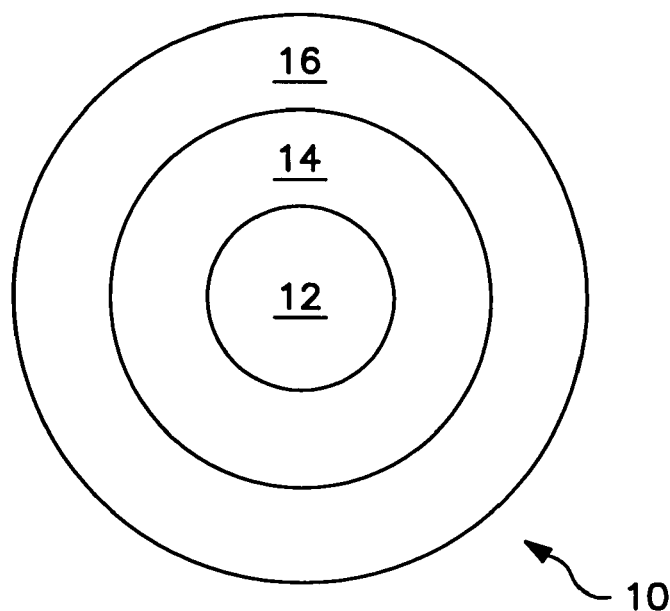
FIG. 1
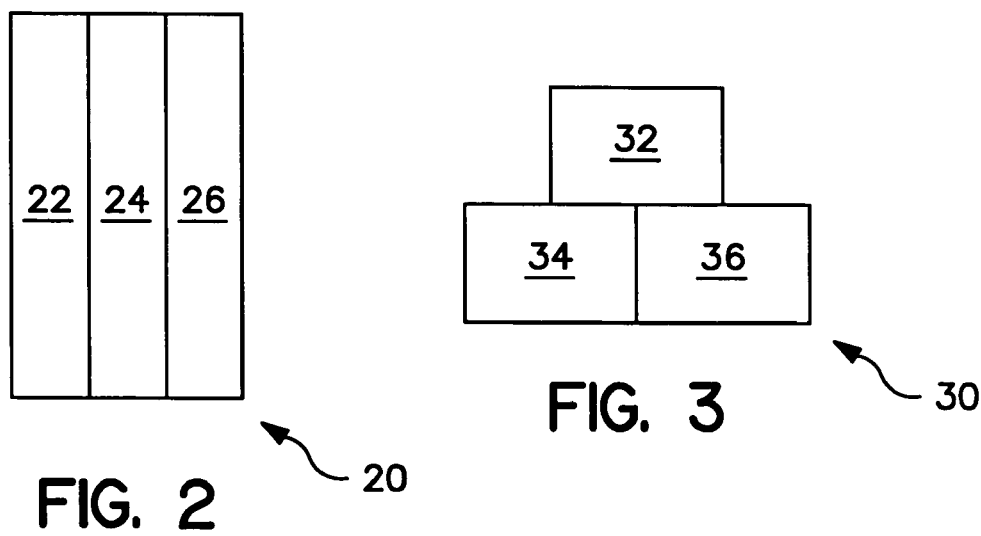
FIG. 2
FIG. 3

42 — CAUTION
44 — WARNING
46 — EMERGENCY
40 ⬈
FIG. 4
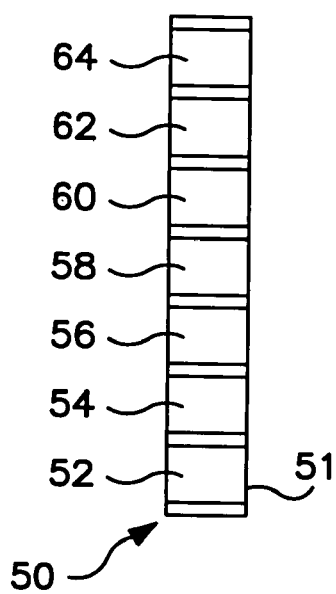
FIG. 5
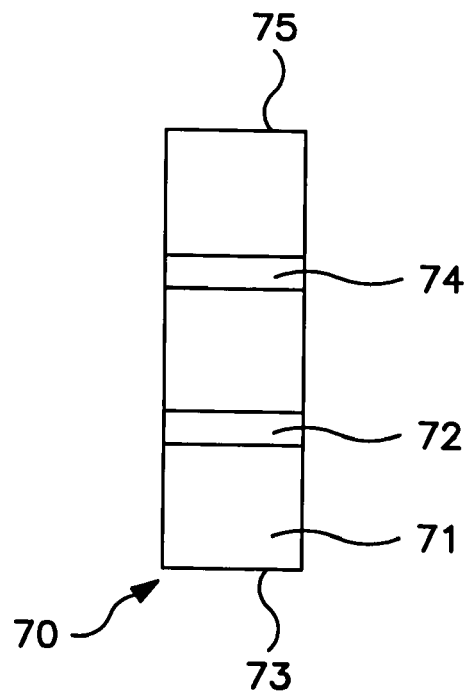
FIG. 6

WEARABLE ARTICLE WITH MULTI-LEVEL ALERT SYSTEM

FIELD OF THE INVENTION

This invention relates to a wearable article with a multi-level alert system for detecting different levels of mammalian substances and conveying the information to a wearer or a care provider.

BACKGROUND OF THE INVENTION

Wearable articles having alert systems are known which detect the presence of blood and other substances in feces, urine and other extracts from a wearer. These alert systems generally fall into two categories. A first category of alert systems is designed to detect any amount, no matter how small, of a mammalian substance such as blood which is not normally present in various mammalian extracts. A second category of alert systems is designed to detect any abnormally high amount of a mammalian substance such as glucose which is usually found in mammalian extracts only within a normal range.

Typically, the alert systems include a chemical detection system which responds to any amount, or an abnormally high amount of a substance by producing a color change or other visual indication in an affected portion of the wearable article. While these alert systems are useful for detecting an abnormal condition, they provide no indication of the severity of the condition. For instance, an alert system for detecting blood in an extract may provide the same color change in response to a trace amount of blood or a higher amount. An alert system for detecting an abnormal level of glucose in an extract may produce the same color change whether the glucose level is barely abnormal or substantially abnormal.

There is a need or desire for wearable articles having alert systems which not only detect abnormalities in mammalian extracts, but which also indicate a level or degree of the abnormality.

SUMMARY OF THE INVENTION

The present invention is directed to a wearable article having a multi-level alert system for detecting abnormalities in fluid extracts. The multi-level alert system includes a multi-level chemical detection system which detects two or more abnormal levels of substances in a mammalian extract, and provides a signal which is commensurate with the abnormal level of the substance.

The wearable article may be an absorbent or non-absorbent garment, headband, bandage, ear plug, or any article which comes into contact with a wearer.

The mammalian extract being tested may be urine, feces, perspiration, blood, menses, ear wax, or any other substance which may be extracted from a human being or other mammal under certain normal conditions.

The mammalian substance being detected may be any substance not normally found in a particular mammalian extract, or abnormal levels of any substance typically found in a mammalian extract at a normal level. Exemplary mammalian substances include hydrogen ion, ion aggregate (i.e., total ion concentration), nitrite, leucocytes, glucose, ketones, blood, phenylanaline, bilirubin, urobilinogen, protein, albumin, specific enzymes, and drugs.

The abnormal levels of substance being detected include at least a first level and a second level. The first level may be anything greater than zero (e.g., when detecting blood in urine) or may be anything greater than a normal level (e.g., when detecting glucose in menses). The second level is greater than the first level. Subsequent (e.g., third, fourth and fifth) levels, if detected, are successively greater than the second level.

The signal may be a first color change at the first abnormal level, a second color change at the second abnormal level, and so on. Different visual and audio signals may also be provided when different abnormal levels of a substance are detected.

With the foregoing in mind, it is a feature and advantage of the invention to provide a wearable article which detects different abnormal levels of substances in mammalian extract, and communicates the severity of the abnormality to a wearer.

BRIEF DESCRIPTION OF THE DRAWINGS

FIG. 1 illustrates a multi-level alert system useful in the invention.

FIGS. 2-4 illustrate different configurations of the multi-level alert system of FIG. 1.

FIGS. 5 and 6 illustrate different embodiments of multi-level alert systems useful in the invention.

DEFINITIONS

"Absorbent article" refers to diapers, training pants, adult incontinence articles, absorbent swimwear, feminine hygiene articles, and the like, otherwise known as personal care absorbent articles. The term also includes bandages, wound dressings, and the like, otherwise known as medical absorbent articles. The term also includes headbands, sweat pants, sweatshirts, athletic socks and the like, otherwise known as athletic absorbent articles.

"Wearable article" refers to absorbent and non-absorbent articles which may come into contact with a mammalian extract from the wearer. The term includes absorbent articles listed above, as well as ear plugs, garments, gowns, caps, aprons and the like which may be non-absorbent in nature.

"Mammalian extract" refers to any fluid-containing matter which is extracted through the skin or through any opening in a mammal. The term includes, without limitation, urine, feces, perspiration, blood, menses, vaginal discharge, ear wax and the like.

"Substance being detected" includes any mammalian substance not normally found in the mammalian extract, and any substance normally found which may be detected at higher or lower than normal levels (i.e., abnormal levels). Exemplary substances are listed above.

"Signal" refers to any visual, audible, or other signal which alerts a wearer distinctively to a first level of a substance being detected, and distinctively to a second higher level of the substance being detected.

DETAILED DESCRIPTION OF THE PRESENTLY PREFERRED EMBODIMENTS

The present invention is a wearable article including a substrate and a multi-level alert system on the substrate for detecting different levels of a mammalian substance in a mammalian extract. The multi-level alert system includes a chemical detection system for detecting a first level of the substance, a second, higher level of the substance, and optionally, additional higher level(s) of the same substance. Optionally, the wearable article may have two or more multi-level alert systems on the same or different substrates, for detecting two or more mammalian substances.

The chemical detection system is placed in a wearable article, suitably in a target area of the wearable article. The "target area" is an area on a substrate which receives or contacts a mammalian extract, and is suitably an area which directly receives or contacts a relatively high concentration of the mammalian extract. For instance, if the wearable article is a personal care absorbent article having a crotch region and front and rear waist region, the target area is suitably located in a crotch region of the absorbent article. If the wearable article is a bandage, the target area is suitably in the center of the bandage. If the wearable article is an athletic sweatshirt, the target area may be any area which receives a predominant stream of perspiration. If the wearable article is an ear plug, the target area is suitably on an inner surface of the ear plug which faces the ear lobe. The chemical detection system can also be incorporated onto a carrier such as a filter paper, which is placed on or inserted in the wearable article.

A typical personal care absorbent article includes a liquid permeable bodyside liner, a liquid impermeable (desirably, water vapor breathable) outer cover, and an absorbent core between them. The target area should include a layer that is visible to the user such as a liner or outer cover.

The chemical detection system may include two or more chemical compositions which are reactive at different levels of the substance being detected. The target area may include two or more sub-areas. A first sub-area may be treated with a first chemical composition that reacts with a first, lower level of the substance being detected to produce a first visual color or other signal. A second sub-area may be treated with a second chemical composition that reacts with a second, higher level of the substance being detected to produce a second visual color or other signal. Similarly, a third sub-area may be treated with a third chemical composition that reacts with a third, still higher level of the substance to produce a third visual color or other signal, and so on. The first, second and third sub-areas may be in any position relative to each other.

FIG. 1 illustrates a multi-level alert system 10, useful to detect blood in a target area of a wearable article. The multi-level alert system 10 includes three concentric sub-areas 12, 14 and 16 of chemical treatments applied in the target area. The sub-area 12 defined by the first (inner) circle contains at least one pouch made of liquid impermeable breakable material which houses at least about 1-2 drops of a working solution. The working solution is made by mixing 2 grams of phenolphthalein, 20 grams of potassium hydroxide, and 100 ml of distilled water, refluxing the mixture with 20 grams of powdered zinc until the solution becomes colorless (2-3 hours), then adding 20 ml of the phenolphthalein solution to 80 ml of absolute ethanol. A 2-compartment pouch with a liquid impermeable breakable dividing wall can also be used wherein one compartment houses at least about 1-2 drops of the working solution and the other compartment contains at least about 1-2 drops of a 3% hydrogen peroxide solution.

Examples of liquid impermeable breakable materials include a wide variety of film forming polymers (e.g. polyolefins, polyamides, polyesters and the like) which can be made thin enough to facilitate breakage under selected conditions. Examples include hot melt encapsulants as described in U.S. Pat. No. 4,063,754, and nylon encapsulants as described in U.S. Pat. No. 4,518,547, both of which are incorporated by reference. The pouch and its dividing wall or other similar encapsulation is broken by applying pressure after use to allow the chemical reagents to react with the bodily fluid in the sub-area 12. Phenolphthalein is a compound made of carbon, hydrogen, and oxygen, having the chemical formula $C_{20}H_{14}O_4$, available from Fisher Scientific, located in Fair Lawn, N.J. Phenolphthalein can detect blood at a concentration of one weight part per 5 million, or 0.2 ppm. In other words, if there is at least one weight part of blood in a solution containing 5 million weight parts of water, phenolphthalein will detect the blood and emit a bright pink color.

Alternatively, a luminol (3-aminophthalhydrazide) working solution can be used in the sub-area 12. The working solution is prepared by mixing 0.5 grams of luminol and 25 grams of sodium carbonate, to this mixture adding a solution of 3.5 grams of sodium perborate in 500 ml of distilled water. The luminol/sodium carbonate mixture and the sodium perborate solution can also be housed separately in a pouch/encapsulation prior to use. Luminol is a compound made of carbon, hydrogen, nitrogen and oxygen, having the chemical formula $C_8H_7N_3O_2$, available from Fisher Scientific, located in Fair Lawn, N.J. Luminol reacts with the iron in hemoglobin, an oxygen-carrying protein in red blood cells. Luminol has similar sensitivity like that of phenolphthalein, and emits a bluish-white luminescence in the dark.

The sub-area 14, defined by the second circle (excluding the sub-area 12 within the first circle) contains at least one pouch made of liquid impermeable breakable material which houses at least about 1-2 drops of an o-tolidine working solution. The working solution is made by adding 1.6 grams of o-tolidine base to 40 ml of absolute ethanol, then adding 30 ml of glacial acid and 30 ml of distilled water. A 2-compartment pouch with a liquid impermeable but breakable dividing wall can also be used wherein one compartment houses at least about 1-2 drops of the o-tolidine working solution and the other compartment contains at least about 1-2 drops of a 3% hydrogen peroxide solution. The pouch and its dividing wall or other similar encapsulation is broken by applying pressure after use to allow the chemical reagents to react with the bodily fluid in the sub-area 14. O-tolidine is a compound having the chemical formula $C_{14}H_{16}N_2$, available from Fisher Scientific, located in Fair Lawn, N.J. O-tolidine can detect blood at a concentration of one weight part per 300,000, or 3.33 ppm. If there is at least one weight part of blood in a solution containing 300,000 weight parts of water, o-tolidine will detect the blood and change to an intense (dark) blue color.

Alternatively, the sub-area 14 can contain at least one pouch made of liquid impermeable but breakable material which houses at least about 1-2 drops of a benzidine working solution made by adding sufficient benzidine base to 2 ml of glacial acetic acid to make a saturated solution, then adding to this 2 ml of 3% hydrogen peroxide. A 2-compartment pouch with a liquid impermeable but breakable dividing wall can also be used wherein one compartment houses at least about 1-2 drops of a benzidine working solution made by dissolving 0.25 grams of benzidine base in 175 ml of absolute ethanol and to this adding about 5-10 drops of glacial acetic acid, and the other compartment contains at least about 1-2 drops of a 3% hydrogen peroxide solution. The pouch and its dividing wall or other similar encapsulation is broken by applying pressure after use to allow the chemical reagents to react with the bodily fluid in the sub-area 14. Benzidine is a compound having the chemical formula $C_{12}H_{12}N_2$, available from Fisher Scientific, located in Fair Lawn, N.J. Benzidine can also detect blood at a concentration of one weight part per 300,000, or 3.33 ppm.

If there is at least one weight part of blood in a solution containing 300,000 weight parts of water, benzidine will detect the blood and change to an intense (dark) blue color.

The sub-area 16 defined by the third circle (excluding the sub-areas 12 and 14 within the first and second circles) contains at least one pouch made of liquid impermeable but breakable material which houses at least about 1-2 drops of a working solution. The working solution is made by adding a leucomalachite green reagent to an acetic acid solution. The leucomalachite green reagent is made by mixing 0.32 grams of sodium perborate thoroughly in a mortar and pestle with 0.1 grams of leucomalachite green. The acetic acid solution is made by diluting 8 ml of acetic acid to 4 ml of distilled water. A 2-compartment pouch with a liquid impermeable but breakable dividing wall can also be used wherein one compartment houses the leucomalachite green reagent and the other compartment contains the acetic acid solution. The pouch and its dividing wall or other similar encapsulation is broken by applying pressure after use to allow the chemical reagents to react with the bodily fluid in the sub-area 16. Alternatively, one of the compartments in sub-area 16 can house at least about 1-2 drops of a leucomalachite solution made by mixing 10 mg of leucomalachite green into 10 ml of the acetic acid solution. The other compartment contains at least about 1-2 drops of 3% solution of hydrogen peroxide. Leucomalachite green is a compound having the chemical formula $C_{23}H_{26}N_2$, available from Fisher Scientific, located in Fair Lawn, N.J. Leucomalachite green can detect blood at a concentration of one weight part per 100,000, or 10 ppm. If there is at least one weight part of blood in a solution containing 100,000 weight parts of water, leucomalachite green will detect the blood and change to an intense (dark) blue-green color.

For indicator systems which use hydrogen peroxide solution, the 3% hydrogen peroxide solution is released or allowed to contact the mammalian substance on the substrate after the other reagents have been exposed to the mammalian substance. This can be achieved by encapsulating the hydrogen peroxide solution in a time-delayed encapsulant or be spraying the hydrogen peroxide solution over the chemical detection system. Time-delayed encapsulants include, without limitation, higher basis weight shell materials which require longer times to dissolve, and temperature-sensitive encapsulants which dissolve more readily at a lower temperature than the mammalian extract insult, and chemically reactive encapsulants which dissolve more slowly in the presence of the mammalian extract insult.

Various other techniques are available for housing or encapsulating the chemical compositions in the first, second and third sub-areas 12, 14 and 16. In one embodiment, conventional microencapsulation technology is employed to provide a large number (e.g., thousands) of the desired chemical compositions in the sub-areas. The microdomains can be encapsulated using water-soluble shells such as shells formed of polyvinyl alcohol, starch, and certain gelatins. The microdomains can be planted in the liner, surge material layer, or absorbent core of an absorbent article, for instance, by blending or spraying the microdomains into the target area of the respective layer. When planted in the absorbent core, the microdomains can be printed or sprayed onto the tissue boundary or the absorbent fluff material. The chemical compositions remain encapsulated in the microdomains until the absorbent article is insulted with a liquid. The liquid insult dissolves the shell material and releases the chemical compositions for interaction with the liquid and detection of a mammalian substance.

When the chemical composition being encapsulated is aqueous, one concern is that the encapsulant might dissolve and prematurely escape a water soluble shell. This concern can be overcome a) by using an excess amount of water soluble encapsulant relative to the material being encapsulated, b) by using a water soluble encapsulant which only dissolves at the slightly elevated temperature of a body fluid insult, and/or c) by using a combination of water soluble and insoluble encapsulants. Combined water soluble and insoluble encapsulants are described in U.S. Pat. Nos. 5,916,969; 6,294,646; and 6,075,118, which are incorporated by reference.

Alternatively, the microdomains can employ a shell material which breaks or bursts under pressure to release the chemical compositions. Also, the microdomains can be applied in a pattern, for example, any of the patterns described below with respect to FIGS. 2-4.

In another embodiment, the chemical compositions in the sub-areas 12, 14 and 16 can be micro-encapsulated, with each interactive ingredient contained in a separate pouch or package that extends around the circumference of the sub-area. Referring to FIG. 1, for instance, each package may be in the form of a circle or tire that fits within the respective sub-area. Barrier materials or seams may be provided within each package in order to separate the interactive ingredients into separate pouches prior to use. Each package material, and barrier material or seam, may be water-soluble or breakable, in response to a liquid insult or pressure. When the package materials, barriers and/or seams dissolve or break, the interactive ingredients within each sub-area combine to form a chemical composition which interacts with the mammalian extract and responds (e.g., by color change) if an abnormal level of a mammalian substance is detected.

Housing of chemicals in each sub-area should not be limited to what is being disclosed here. The different ways being disclosed here are for illustration purposes. Each mixture/solution can be encapsulated or enclosed individually using any known method in order to prevent bodily fluid from contacting the chemicals prior to use. An individually wrapped or encapsulated mixture/solution can also be housed in fluid permeable pouch or one-way fluid permeable pouch as long as the chemicals only either react with bodily fluid and/or with each other at the time determined by the user or caregiver. Examples of controlled release pouch materials include cross linked swellable polymers, such as a cross linked copolymer of alkylacrylate and acrylic acid.

If the target area is exposed to blood in a concentration of 0.2 ppm or greater, the first sub-area 12 will detect the blood and emit color. If the blood concentration is about 3.33 ppm or greater, the second sub-area 14 will also emit a color, which is different than the color in the first sub-area. If the blood concentration is about 10 ppm or greater, the third sub-area 16 will also emit a color, which is different than the colors in the first two sub-areas.

The chemicals in the sub-areas 12, 14 and 16 may be encapsulated in microcapsules in various patterns which are dissolved or broken during or after use of the wearable article, to cause contact between the chemicals and the mammalian substance. Suitable encapsulating materials are described in U.S. Pat. No, 6,541,030, which is incorporated by reference, and include gelatin, polyvinyl alcohol, ethylcellulose, cellulose acetatephthalate, and styrene maleic anhydride.

The sub-areas in the multi-level alert system need not be defined by concentric circles. In the multi-level alert system 20 of FIG. 2, the sub-areas 22, 24 and 26 are arranged within three parallel stripes in the target area. In the multi-level alert system 30 of FIG. 3, the sub-areas 32, 34 and 36 are arranged within three adjacent boxes in the target area of the wearable article. The sub-areas treated with the first, second and third chemicals can also be in the form of shapes, symbols, letters, numbers, or even words that spell out different levels of urgency in seeking medical treatment. Shapes such as squares, circles, rectangles, triangles, diamonds, and the like may form sub-areas which can be adjacent to each other. In the multi-level alert system 40 of FIG. 4, the sub-areas 42, 44 and 46 which contain the three chemical treatments are arranged to spell the words CAUTION, WARNING, and EMERGENCY.

The chemical treatment system can be applied to the sub-areas in the target area of a wearable article by printing, solution coating, spraying, or any other suitable technique. The amount or coating density of each chemical applied should be sufficient to cause a highly visible color change when the substance being detected reaches the detectable concentration. If the chemical coating is too sparse, then the color change may appear faded and difficult to see.

The method and amount of application may also vary depending on the type of substrate in the target area being coated. If the wearable article is a personal care absorbent article which includes a liquid-permeable bodyside liner, a liquid impermeable outer cover and an absorbent core between them, the target area may appear on the bodyside liner. The bodyside liner which receives the chemical treatment system may be formed of an apertured polyolefin film, a polyolefin spunbond web, or another suitable liquid transfer material.

If the wearable article is a headband, sweatshirt, sweatpant, underpant or sock, the chemical treatment system may be formed on the inside or outside of a cloth-like material that forms the wearable article. A chemical treatment system deposited only on the inside of the wearable article may be of sufficient quantity that any color change due to an abnormal amount of a substance in a mammalian extract (e.g., perspiration) is visible from either the inside or the outside of the wearable article. This way, the wearer can be quickly and easily alerted to an abnormal substance level without having to remove the article and inspect its interior. A chemical treatment system deposited only on the outside of the wearable article should be sensitive enough to detect abnormal substance levels based on amounts of mammalian extract that soak all the way through the article.

FIG. 5 illustrates another embodiment of a multi-level alert system, generally designated as 50, which can be incorporated into a target area of a diaper, underpant, shirt or other wearable article and used to detect a pH condition which will or may lead to the development of a rash. The multi-level alert system 50 may include a substrate 51 which is paper, cloth, a fibrous nonwoven material or another suitable material, and which may be absorbent. The substrate 51 can be affixed in a target area of a wearable article for receiving urine, fecal matter, perspiration or another mammalian substance capable of causing rashes.

The substrate 51 may define a plurality of sub-areas, such as the seven sub-areas 52, 54, 56, 58, 60, 62 and 64 illustrated in FIG. 5. Each sub-area may be treated with a different chemical which causes a color change at a different pH. While not wishing to be restricted to any particular theory, materials that help maintain normal skin pH are desirous, as rashes and/or other skin problems are least likely to develop when the wearer's skin surface is at a slightly acidic pH of about 5-6. Rashes have a higher tendency to develop when the wearer's skin is exposed to a more neutral pH of 6-7. Skin rashes have a greater tendency to develop at a slightly basic pH of 7-8, and are still more likely to occur when the skin is exposed to a more basic substance having a pH greater than 8. At the other end of the scale, skin rashes or burns may develop when exposed to a substance having a more acidic pH of 4-5, have a greater tendency to develop at a pH of about 3-4, and are still more likely to occur at a pH less than 3.

Referring to FIG. 5, the first sub-area 52 may be treated with a first chemical, 0.04% thymol blue, which changes to a deep red color at a pH of 1.2 to 2.8. As an alternative to a mere color change, the first sub-area or an adjacent region may also display the word "EMERGENCY" when exposed to a substance having that pH.

The second sub-area 54 may be treated with a second chemical, 0.04% bromophenol blue, which changes to a red color at a pH between 3.0 and 4.6. Alternatively or additionally, the second sub-area or an adjacent region may display the word "WARNING" at that pH.

The third sub-area 56 may be treated with a third chemical, 0.04% bromocresol green, which changes to a pink color at a pH between 3.8 and 5.4. Alternatively or additionally, the third sub-area or an adjacent region may display the word "CAUTION" at that pH.

The fourth sub-area 58 may be treated with a fourth chemical, 0.04% methyl red, which emits a light pink color at a pH between 4.4 and 6.2. Alternatively or additionally, the fourth sub-area or an adjacent region may display the word "NORMAL" at that pH.

The fifth sub-area 60 may be treated with a fifth chemical, 0.04% bromothymol blue, which emits no color at a pH of 6.0 to 7.6. Alternatively or additionally, the fifth sub-area or an adjacent region may display the word "CAUTION" at that pH.

The sixth sub-area 62 may be treated with a sixth chemical, 0.02% phenol red, which changes to a light blue color at a pH of 6.8 to 8.2. Alternatively or additionally, the sixth sub-area or an adjacent region may display the word "WARNING" at that pH.

The seventh sub-area 64 may be treated with a seventh chemical, 0.04% thymol blue, which changes to a deep blue color at a pH of 8.0 to 9.2. Alternatively or additionally, the seventh sub-area or an adjacent region may display the word "EMERGENCY" at that pH.

Paper intended for measuring pH using this scale and these chemicals can be obtained from Fisher Scientific Co. The pH paper can be inserted into a target area of a wearable article, in accordance with the invention. Alternatively, the pH-sensitive chemicals in each sub-area may be printed onto the substrate to indicate the words "NORMAL," "CAUTION," "WARNING" or "EMERGENCY." The area surrounding each word may be printed with a non-reactive ink or other substance having the same color as the unreacted pH-sensitive chemical in that sub-area. This way, the words are not visible until an insult with a mammalian extract causes one or more of the pH sensitive chemicals to change color, exposing the words.

FIG. 6 illustrates another embodiment of a multi-level alert system, generally designated as 70, which can be incorporated into a target area of a diaper, training pant, underpant, adult incontinence article or the like. The multi-level alert system 70 embodies a technology similar to a urinary albumin detector known as IMMUNODIP®, available from Diagnostic Chemicals Ltd. of Oxford, Conn. The primary difference is that the IMMUNODIP® instrument is designed for dipping into urine, and is not incorporated into a wearable article.

The multi-level alert system 70, useful for an early detection of kidney disease, includes a substrate 71 which can be paper, cloth, a fibrous nonwoven material or the like. A first end 73 of substrate 71 is placed in a target area for receiving urine, which then migrates from first end 73 toward second end 75. The substrate 71 includes two spaced apart bands defining a first sub-area 72 and a second sub-area 74. The first sub-area 72 is treated with a first chemical, which can be an immobilized human serum albumin. The second sub-area 74 is treated with a second chemical, which can be an immobilized anti-mouse antibody. The substrate is also treated with a conjugate, such as colloidal gold or colored latex particles as described in U.S. Pat. No. 6,001,658, which is incorporated by reference.

At albumin concentrations of less than 12 mg per liter of urine, the first and second sub-areas 72 and 74 display a color, which can be a cranberry color, and the color in the first sub-area 72 is darker than the color in the second sub-area 74. At albumin concentrations between 12-18 mg per liter, the color in the first sub-area 72 and in the second sub-area 74 have roughly an equal shade of darkness. At albumin concentrations greater than 18 mg per liter and less than 80 mg per liter, the color in the second sub-area 74 is darker than in the first sub-area 72, with the latter becoming progressively lighter, at higher albumin concentrations. At albumin concentrations of 80 mg per liter and higher, only the second sub-area 74 is colored, and the first sub-area 72 is devoid of the color. The color is caused by binding of the urinary albumin to the conjugate, migration of the conjugate and subsequent interaction of the conjugate with the chemicals in the sub-areas 72 and 74. The migration and interaction of the conjugate are further described in the above-mentioned U.S. Pat. No. 6,001,658. In order to facilitate entry of the urine at the first end 73 and subsequent migration toward the second end 75, the alert system 70 can be encapsulated so that only the first end 73 is exposed.

In the embodiments described thus far, each signal provided by the multi-level alert system is a color change, with different colors occurring at different levels of the substance being detected. The multi-level alert system may also be provided with different visual, audio, or other signals occurring at different levels of the substance being detected. For instance, an electrical circuit may be provided which detects and communicates changing characteristics of the chemical compositions deposited in different sub-areas of the target area of a wearable article. The changing characteristics may include thermal emissions, changes in ionic concentrations, changes in electrical conductivity or the like, which occur in response to different levels of the substance being detected. The changing characteristics of the chemical compositions can be used to generate an electrical signal which is analyzed and passed to a light emitting diode panel, which generates different amounts or color of light depending on the strength of the signal. Alternatively, the electrical signal can be analyzed and passed to a small speaker which emits different amounts or types of sound depending on the strength of the signal. The electrical signal can be in the form of a change in conductivity through the chemically treated area of the garment, due to a chemical reaction with the substance being detected. The electrical circuit can be powered using a watch battery, solar cell or the like.

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

We claim:

1. A wearable article equipped with a multi-level alert system for detecting two or more levels of a mammalian substance in a mammalian extract, the wearable article comprising:
    a substrate;
    a target area on the substrate including first and second sub-areas for receiving the mammalian extract; and
    a chemical detection system on the target area for detecting at least a first lower level of the mammalian substance in the first sub-area and a second higher level of the mammalian substance in the second sub-area;
    wherein the chemical detection system comprises a first chemical composition on the first sub-area and a second chemical composition on the second sub-area, the first chemical composition detects the first lower level of the mammalian substance and the second chemical composition detects the second higher level of the mammalian substance; and
    the mammalian substance being detected is not a hydrogen ion or ion aggregate.

2. The wearable article of claim 1, wherein the first chemical composition emits a first color to indicate detection of the first lower level of the mammalian substance, and the second chemical composition emits a second color to indicate detection of the second higher level of the mammalian substance.

3. The wearable article of claim 1, wherein the target area further comprises a third sub-area, and the chemical detection system further comprises a third chemical composition on the third sub-area for detecting a third level of the mammalian substance.

4. The wearable article of claim 3, wherein the first chemical composition emits a first color to indicate detection of the first level of mammalian substance, the second chemical composition emits a second color to indicate detection of the second level of mammalian substance, and the third chemical composition emits a third color to indicate detection of the third level of mammalian substance.

5. The wearable article of claim 1, wherein the wearable article is a personal care absorbent article.

6. The wearable article of claim 1, wherein the wearable article is a medical absorbent article.

7. The wearable article of claim 1, wherein the wearable article is an athletic absorbent article.

8. The wearable article of claim 1, wherein the wearable article is a nonabsorbent article.

9. A wearable article equipped with a multi-level alert system for detecting two or more levels of a mammalian substance in a mammalian extract, the wearable article comprising:
    a substrate;
    a target area on the substrate including first and second sub-areas for receiving the Mammalian extract; and
    a chemical detection system on the target area which initiates a first signal in response to a first level of the mammalian substance in the first sub-area and a second signal in response to a second level of the mammalian substance in the second sub-area;
    wherein the chemical detection system comprises a first chemical composition on the first sub-area and a second chemical composition on the second sub-area, the first chemical composition detects the first lower level of the mammalian substance and the second chemical composition detects the second higher level of the mammalian substance; and the mammalian substance being detected is not a hydrogen ion or ion aggregate.

10. The wearable article of claim 9, wherein the first signal comprises a first color change in the first sub-area and the second signal comprises a second color change in the second sub-area.

11. The wearable article of claim 9, wherein the first signal comprises a first light and the second signal comprises a second light.

12. The wearable article of claim 9, wherein the first signal comprises a first sound and the second signal comprises a second sound.

13. The wearable article of claim 9, wherein the target area includes a third sub-area, and the chemical detection system initiates a third signal in response to a third level of mammalian substance in the third sub-area.

14. The wearable article of claim 9, wherein the wearable article is a personal care absorbent article.

15. The wearable article of claim 9, wherein the wearable article is a garment.

16. The wearable article of claim 9, wherein the wearable article is a medical absorbent article.

17. The wearable article of claim 9, wherein the wearable article is an article of clothing.

18. The wearable article of claim 9, wherein the wearable article is a nonabsorbent article.

19. A wearable article equipped with a multi-level alert system for detecting three or more levels of a mammalian substance in a mammalian extract, the wearable article comprising:

a substrate;

a target area on the substrate including first, second and third sub-areas for receiving the mammalian extract;

a first chemical composition on the first sub-area, which detects a first level of the mammalian substance;

a second chemical composition on the second sub-area, which detects a second level of the mammalian substance; and a third chemical composition on the third sub-area, which detects a third level of the mammalian substance;

wherein the mammalian substance being detected is not a hydrogen ion or ion aggregate.

20. The wearable article of claim 19, wherein the first, second and third sub-areas comprise concentric shapes.

21. The wearable article of claim 19, wherein the first, second and third sub-areas comprise stripes.

22. The wearable article of claim 19, wherein the first, second and third sub-areas comprise adjacent shapes selected from the group consisting of squares, circles, rectangles, triangles, diamonds, and combinations thereof.

23. The wearable article of claim 19, wherein the first, second and third sub-areas comprise numbers, symbols, letters or words.

24. The wearable article of claim 19, wherein the first chemical composition comprises phenolphthalein, the second chemical composition comprises o-tolidine, and the third chemical composition comprises leucomalachite.

25. The wearable article of claim 19, wherein the mammalian substance comprises blood, and the chemical compositions in the sub areas are adapted to detect different levels of the blood.

26. A wearable article equipped with a multi-level alert system for detecting two or more levels of a mammalian substance in a mammalian extract comprising:

a substrate;

a target area on the substrate including first and second sub-areas for receiving the mammalian extract;

a first chemical composition on the first sub-area which emits a first signal in response to a first level of the mammalian substance; and a second chemical composition on the second sub-area which emits a second signal in response to the first level of the mammalian substance;

wherein the first and second signals can be compared to quantify the first level of the mammalian substance; and the mammalian substance being detected is not a hydrogen ion or ion aggregate.

* * * * *